(12) United States Patent
Iwata et al.

(10) Patent No.: US 9,241,485 B2
(45) Date of Patent: *Jan. 26, 2016

(54) COMPOSITION AND METHOD FOR CONTROLLING HARMFUL ARTHROPODS

(71) Applicant: SUMITOMO CHEMICAL COMPANY, LIMITED, Tokyo (JP)

(72) Inventors: Atsushi Iwata, Tokyo (JP); Tatsuya Suzuki, Hyogo (JP); Chie Shimizu, Hyogo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 23 days.

This patent is subject to a terminal disclaimer.

(21) Appl. No.: 14/350,177

(22) PCT Filed: Dec. 5, 2012

(86) PCT No.: PCT/JP2012/082117
§ 371 (c)(1),
(2) Date: Apr. 7, 2014

(87) PCT Pub. No.: WO2013/085065
PCT Pub. Date: Jun. 13, 2013

(65) Prior Publication Data
US 2014/0288131 A1    Sep. 25, 2014

(30) Foreign Application Priority Data
Dec. 8, 2011  (JP) .................. 2011-268613

(51) Int. Cl.
*A01N 37/30* (2006.01)
*A01N 43/56* (2006.01)

(52) U.S. Cl.
CPC ............... *A01N 37/30* (2013.01); *A01N 43/56* (2013.01)

(58) Field of Classification Search
CPC ... A01N 37/30; A01N 43/56; A01N 2300/00; A01N 25/00
See application file for complete search history.

(56) References Cited

U.S. PATENT DOCUMENTS

2012/0135863 A1    5/2012  Murakami et al.

FOREIGN PATENT DOCUMENTS

| JP | 11-255607 | 9/1999 |
|---|---|---|
| JP | 2001-139405 | 5/2001 |
| JP | 4087942 | 5/2008 |
| WO | 2011/062291 | 5/2011 |
| WO | 2013/085065 | 6/2013 |
| WO | 2013/085067 | 6/2013 |
| WO | 2013/085068 | 6/2013 |
| WO | 2013/085069 | 6/2013 |
| WO | 2013/085070 | 6/2013 |

OTHER PUBLICATIONS

CDS Tomlin, ed., The Pesticide Manual, 15th edition, BCPC, ISBN 978-1-901396-18-8, pp. 175, 176, 251, 1400 and 1403, 2009.
International Search Report issued Feb. 19, 2013 in International (PCT) Application No. PCT/JP2012/082117.

*Primary Examiner* — Savitha Rao
(74) *Attorney, Agent, or Firm* — Wenderoth, Lind & Ponack, L.L.P.

(57) ABSTRACT

The present invention provides a composition for controlling harmful arthropods having an excellent control efficacy on harmful arthropods. A composition for controlling harmful arthropods comprising an amide represented by a formula (I) wherein each of symbols are the same as defined in the Description; or salts thereof and at least one kind of pyrazole compounds selected from the group (A) consisting of chlorantraniliprole, cyantraniliprole and a compound represented by a formula (II), shows an excellent controlling efficacy on harmful arthropods.

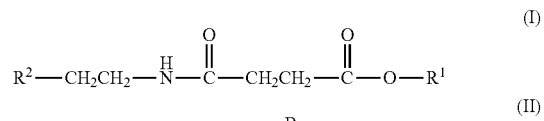

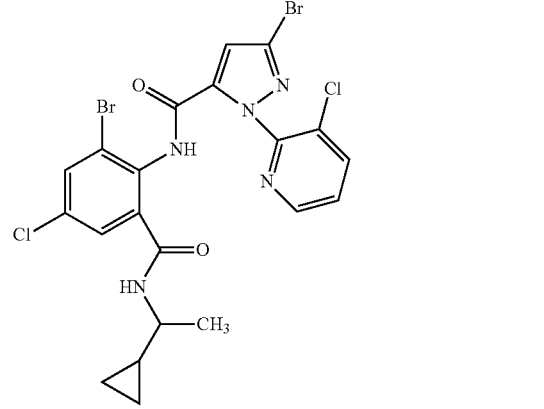

4 Claims, No Drawings

COMPOSITION AND METHOD FOR CONTROLLING HARMFUL ARTHROPODS

TECHNICAL FIELD

The present invention relates to a composition for controlling harmful arthropods and a method for controlling harmful arthropods.

BACKGROUND ART

Hitherto, many, compounds have been known as active ingredients in a composition for controlling harmful arthropods (The Pesticide Manual-15th edition, published by British Crop Protection Council (BCPC), ISBN978-1-901396-18-8).

DISCLOSURE of INVENTION

Problems to be Solved by Invention

An object of the present invention is to provide a composition for controlling harmful arthropods having an excellent control efficacy on harmful arthropods.

Means to Solve Problems

The present inventors have intensively studied to find out a composition for controlling harmful arthropods having an excellent control efficacy on harmful arthropods. As a result, they have found that a composition comprising an amide compound represented by the following formula (I) or salts thereof and at least one kind of compounds selected from the group consisting of the following group (A) has an excellent controlling effect on harmful arthropods. Thus, the present invention has been completed.

Specifically, the present invention includes:

[1] A composition for controlling harmful arthropods comprising an amide represented by a formula (I);

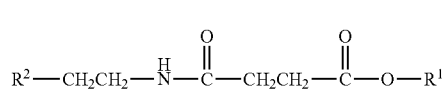

(I)

$R^1$ represents a C1-C6 alkyl group;

$R^2$ represents an optionally substituted phenyl group, an optionally substituted 1-naphthyl group or an optionally substituted 3-indolyl group, and the phenyl group, the 1-naphthyl group or the 3-indolyl group being represented by the $R^2$ may be substituted on the carbon atoms independently of each other with one or more substituents selected from a halogen atom, a hydroxyl group, a nitro group, a C1-C6 alkyl group or a C1-C6 alkoxy group;

or salts thereof and at least one kind of pyrazole compounds selected from the group (A) consisting of chlorantraniliprole, cyantraniliprole and a compound represented by a formula (II).

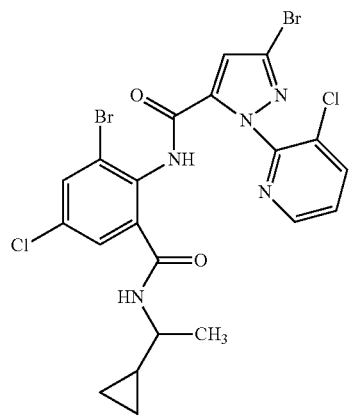

(II)

[2] The composition for controlling harmful arthropods according to [1] wherein a weight ratio of the amide compound or salts thereof to the pyrazole compounds selected from the group (A) is in the range of 100:1 to 1:100.

[3] A method for controlling harmful arthropods which comprises applying an effective amount of the composition for controlling harmful arthropods according to [1] or [2] to harmful arthropods or a place where the harmful arthropods live.

[4] A method for controlling harmful arthropods which comprises applying an effective amount of the composition for controlling harmful arthropods according to [1] or [2] to plant seeds.

[5] The method for controlling harmful arthropods according to [4] wherein the plant seeds are seeds of corn, cotton, soybean, beet, rapeseed or rice.

Effect of Invention

The present invention can control harmful arthropods.

MODE FOR CARRYING OUT THE INVENTION

Hereinafter, the present invention is explained in detail.

The term "composition for controlling harmful arthropods of the present invention" refers to a composition comprising an amide compound represented by a formula (I):

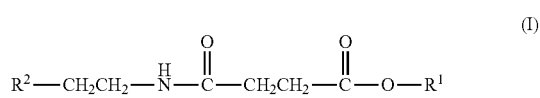

(I)

wherein $R^1$ represents a C1-C6 alkyl group;

$R^2$ represents an optionally substituted phenyl group, an optionally substituted 1-naphthyl group or an optionally substituted 3-indolyl group, and the phenyl group, the 1-naphthyl group or the 3-indolyl group being represented by the $R^2$ may be substituted on the carbon atoms independently of each other with one or more substituents selected from a halogen atom, a hydroxyl group, a nitro group, a C1-C6 alkyl group or a C1-C6 alkoxy group (hereinafter referred as to "the present amide compound");

or salts thereof and at least one kind of pyrazole compounds selected from the group (A) consisting of chlorantraniliprole, cyantraniliprole and a compound represented by a formula (II) (hereinafter referred as to "the present pyrazole compounds").

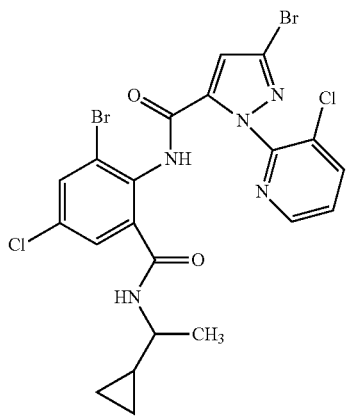

In the formula (I), as the group represented by the $R^1$, the term "C1-C6 alkyl group" includes, for example, a methyl group, an ethyl group, a propyl group, a butyl group, a pentyl group, a hexyl group, a 1-methylethyl group, a 2-methylpropyl group, a 3-methylbutyl group and a 4-methylpentyl group.

In the formula (I), when the phenyl group, the 1-naphthyl group or the 3-indolyl group being represented by the $R^2$ may be substituted on the carbon atoms independently of each other with one or more substituents (preferably one or two substituents and more preferably one substituent), as the substituent, the term "halogen atom" includes, for example, a fluorine atom, a chlorine atom, a bromine atom and an iodine atom;

the term "C1-C6 alkyl group" includes, for example, a methyl group, an ethyl group, a propyl group, a butyl group, a pentyl group, a hexyl group, a 1-methylethyl group, a 2-methylpropyl group, a 3-methylbutyl group and a 4-methylpentyl group;

the term "C1-C6 alkoxy group" includes, for example, a methoxy group, an ethoxy group, a propoxy group, a butoxy group, a pentyloxy group, a hexyloxy group, a 1-methylethoxy, a 2-methylpropoxy group, a 3-methylbutoxy group and a 4-methylpentyloxy group.

When in the formula (I), the phenyl group, the 1-naphthyl group or the 3-indolyl group being represented by the $R^2$ may be substituted on the carbon atoms simultaneously with each other with two or more substituents selected from the halogen atom, the hydroxyl group, the nitro group, the C1-C6 alkyl group or the C1-C6 alkoxy group, the substituent on each of the carbon atoms may be the same or different to each other.

Examples of the present amide compound include as follows:

the amide compound represented by formula (I) wherein $R^1$ is a C1-C3 alkyl group, and $R^2$ is a phenyl group, a 1-naphthyl group, an 3-indolyl group or a 5-methyl-3-indolyl group; and the amide compound represented by formula (I) wherein $R^1$ is a C1-C3 alkyl group, and $R^2$ is a phenyl group which may be substituted with one or more halogen atoms.

The salts of the present amide compound include, for example, inorganic base salts and organic base salts.

The inorganic base salts include, for example, alkali metal salts such as sodium salts and potassium salts, alkaline-earth metal salts such as calcium salts and magnesium salts, and ammonium salts.

The organic base salts include, for example, amine salts such as triethylamine salts, pyridine salts, picoline salts, ethanolamine salts, triethanolamine salts, dicyclohexylamine salts, and N,N'-dibenzylethylenediamine salts.

Next, specific examples of the present amide compound are shown below.

The amide compound represented by the formula (I-a):

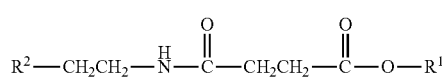

wherein a combination of $R^1$ and $R^2$ represents any combination as shown in Table 1.

TABLE 1

| Compound No. | $R^1$ | $R^2$ |
|---|---|---|
| 1 | methyl | phenyl |
| 2 | ethyl | phenyl |
| 3 | propyl | phenyl |
| 4 | 2-methylethyl | phenyl |
| 5 | methyl | 4-fluorophenyl |
| 6 | methyl | 4-chlorophenyl |
| 7 | methyl | 4-bromophenyl |
| 8 | methyl | 4-iodophenyl |
| 9 | methyl | 2-chlorophenyl |
| 10 | methyl | 3-chlorophenyl |
| 11 | methyl | 3,4-dichlorophenyl |

The present amide compounds are those described in, for example, JP-11-255607 A and JP-2001-139405 A, and can be prepared, for example, according to the methods described therein.

Also, chlorantraniliprole and cyantraniliprole that used in the present invention are all known compounds, and are described in, for example, "The PESTICIDE MANUAL-15th EDITION (BCPC published) ISBN 978-1-901396-18-8", pages 175 and 251 respectively. These compounds are either commercially available, or can be prepared by known methods.

The compound represented by the formula (II) is described in JP-2004-238307 A, and can be prepared, for example, according to the methods described therein.

The weight ratio of the present amide compound or salts thereof to the present pyrazole compounds in the composition for controlling harmful arthropods of the present invention includes, but is not limited to, in the range of usually 2 to 10,000,000 parts by weight, preferably 10 to 100,000 parts by weight, more preferably 100 to 10,000 parts by 15, weight, and further preferably 500 to 10,000 parts by weight of the present pyrazole compounds opposed to 1,000 parts by weight of the present amide compound or salts thereof.

Although the composition for controlling harmful arthropods of the present invention may be a mixture as itself of the present amide compound or salts thereof and the present pyrazole compounds, the composition of the present invention is usually prepared by mixing the present amide compound or salts thereof, the present pyrazole compounds and an inert carrier, and if necessary, adding a surfactant or other pharmaceutical additives, and then formulating into the form of oil solution, emulsifiable concentrate, flowable formulation, wettable powder, granulated wettable powder, dust formulation, granules and so on.

Also the composition for controlling harmful arthropods formulated as aforementioned can be used by itself or with an addition of other inert components as agent for controlling harmful arthropods.

In the composition for controlling harmful arthropods of the present invention, a total amount of the present amide compound or salts thereof and the present pyrazole compounds is in the range of usually 0.1% to 99% by weight, preferably 0.2% to 90% by weight, and more preferably 1% to 80% by weight.

Also the composition for controlling harmful arthropods of the present invention may further optionally contain one or more pesticides and/or fungicides other than those mentioned above.

Examples of the inert carrier used in the formulation include an inert solid carrier and an inert liquid carrier.

Examples of a solid carrier used in the formulation include finely-divided power or particles of clay consisting of minerals (for example, kaolin clay, attapulgite clay, bentonite, montmorillonite, acid clay, pyrophyllite, talc, diatomaceous earth, or calcite), natural organic substances (for example, corncob powder, or walnut shell powder), synthetic organic substances (for example, urea), salts (for example, calcium carbonate, or ammonium sulfate), synthetic inorganic substances (for example, synthetic hydrous silicon oxide) and the others. Examples of a liquid carrier include aromatic hydrocarbons (for example, xylene, alkyl benzene, or methylnaphtalene), alcohols (for example, 2-propanol, ethylene glycol, propylene glycol, or ethylene glycol monoethyl ether), ketones (for example, acetone, cyclohexanone, or isophorone), vegetable oils (for example, soybean oil, or cotton oils), petroleum-derived aliphatic hydrocarbons, esters, dimethylsulfoxide, acetonitrile and water.

Examples of the surfactant include anionic surfactant (for example, alkyl sulfate salts, alkylaryl sulfate salts, dialkyl sulfosuccinate salts, polyoxyethylene alkylaryl ether phosphates, lignin sulfonate, or naphthalenesulfonate formaldehyde polycondensation), nonionic surfactant (for example, polyoxyethylene alkylaryl ether, polyoxyethylene alkyl polyoxypropylene block copolymer, or sorbitan fatty acid ester) and cationic surfactant (for example, alkyltrimethyl ammonium salts).

Examples of the other pharmaceutical additives include water-soluble polymer (for example, polyvinyl alcohol, or polyvinyl pyrrolidone), polysaccharides (for example, arabic gum, alginic acid and salts thereof, CMC (carboxymethylcellulose), or xanthan gum), inorganic substances (for example, aluminum magnesium silicate, or alumina-sol), antiseptic agent, coloring agent, and PAP (isopropyl acid phosphate), and stabilizing agent (for example, BHT).

The composition for controlling harmful arthropods of the present invention can be used for protecting plants from damage due to eating or sucking or the like by harmful arthropods.

The harmful arthropods on which the composition for controlling harmful arthropods of the present invention has a controlling efficacy is exemplified below:

Hemiptera:
Delphacidae (for example, *Laodelphax striatellus*, *Nilaparvata lugens*, and *Sogatella furcifera*),
Deltocephalidae (for example, *Nephotettix cincticeps*, and *Nephotettix virescens*),
Aphididae (for example, *Aphis gossypii*, *Myzus persicae*, *Brevicoryne brassicae*, *Macrosiphum euphorbiae*, *Aulacorthum solani*, *Rhopalosiphum padi*, and *Toxoptera citricidus*),
Pentatomidae (for example, *Nezara antennata*, *Riptortus clavetus*, *Leptocorisa chinensis*, *Eysarcoris parvus*, *Halyomorpha mista*, and *Lygus lineolaris*),
Aleyrodidae (for example, *Trialeurodes vaporariorum*, *Bemisia tabaci*, and *Bemisia argentifolii*), and the others;

Lepidoptera:
Pyralidae (for example, *Chilo suppressalis*, *Tryporyza incertulas*, *Cnaphalocrocis medinalis*, *Notarcha derogata* *Plodia interpunctella*, *Ostrinia furnacalis*, *Ostrinia nubilaris*, *Hellula undalis*, and *Pediasia teterrellus*),
Noctuidae (for example, *Spodoptera litura*, *Spodoptera exigua*, *Pseudaletia separata*, *Mamestra brassicae*, *Agrotis ipsilon*, *Plusia nigrisigna*, *Trichoplusia* spp., *Heliothis* spp., and *Helicoverpa* spp.),
Pieridae (for example, *Pieris rapae*),
Tortricidae (for example, *Adoxophyes* spp., *Grapholita molesta*, *Leguminivora glycinivorella*, *Matsumuraeses azukivora*, *Adoxophyes orana fasciata*, *Adoxophyes* sp., *Homona magnanima*, *Archips fuscocupreanus*, and *Cydia pomonella*),
Gracillariidae (for example, *Caloptilia theivora*, and *Phyllonorycter ringoneella*),
Carposinidae (for example, *Carposina niponensis*),
Lyonetiidae (for example, *Lyonetia* spp.),
Lymantriidae (for example, *Lymantria* spp., and *Euproctis* spp.),
Yponomeutidae (for example, *Pluteila xylostella*),
Gelechiidae (for example, *Pectinophora gossypiella*, and *Phthorimaea operculella*),
Arctiidae (for example, *Hyphantria cunea*),
Tineidae (for example, *Tinea translucens*), and the others;

Thysanoptera:
Thripidae (for example, *Frankliniella occidentalis*, *Thrips parmi*, *Scirtothrips dorsalis*, *Thrips tabaci*, *Frankliniella intonsa*, and *Frankliniella fusca*), and the others;

Diptera:
Agromyzidae (for example, *Hylemya antiqua*, *Hylemya platura*, *Agromyza oryzae*, *Hydrellia griseola*, *Chlorops oryzae*, and *Liriomyza trifolii*),
*Dacus cucurbitae*, *Ceratitis capitata*, and the others;

Coleoptera:
*Epilachna vigintioctopunctata*, *Aulacophora femoralis*, *Phyllotreta striolata*, *Oulema oryzae*, *Echinocnemus squameus*, *Lissorhoptrus oryzophilus*, *Anthonomus grandis*, *Callosobruchus chinensis*, *Sphenophorus venatus*, *Popillia japonica*, *Anomala cuprea*, *Diabrotica* spp., *Leptinotarsa decemlineata*, *Agriotes* spp., *Lasioderma serricorne* and the others;

Orthoptera:
*Gryllotalpa africana*, *Oxya yezoensis*, *Oxya japonica* and the others.

The composition for controlling harmful arthropods of the present invention can be used in agricultural lands such as fields, paddy fields, dry paddy fields, lawns and orchards or in non-agricultural lands. Also the composition for controlling harmful arthropods of the present invention can control harmful arthropods that live in agricultural lands in the agricultural lands and the others for cultivating the following "plant" and the others.

The plant which can be applied by the composition for controlling for harmful arthropods of the present invention is exemplified below:

Crops:
corn, rice, wheat, barley, rye, oat, sorghum, cotton, soybean, peanut, buckwheat, beet, rapeseed, sunflower, sugar cane, tobacco, and the others;

Vegetables:
solanaceous vegetables (for example, eggplant, tomato, pimento, pepper and potato),
cucurbitaceous vegetables (for example, cucumber, pumpkin, zucchini, water melon and melon),
cruciferous vegetables (for example, Japanese radish, white turnip, horseradish, kohlrabi, Chinese cabbage, cabbage, leaf mustard, broccoli, cauliflower, colza),
asteraceous vegetables (for example, burdock, crown daisy, artichoke and lettuce),
liliaceous vegetables (for example, green onion, onion, garlic and asparagus),
ammiaceous vegetables (for example, carrot, parsley, celery and parsnip),
chenopodiaceous vegetables (for example, spinach and Swiss chard),
lamiaceous vegetables (for example, *Perilla frutescens*, mint and basil),
strawberry, sweet potato, *Dioscorea japonica*, colocasia and the others;

Fruits:
pomaceous fruits (for example, apple, pear, Japanese pear, Chinese quince and quince),
stone fleshy fruits (for example, peach, plum, nectarine, *Prunus mume*, cherry fruit, apricot and prune), citrus fruits (for example, *Citrus unshiu*, orange, lemon, lime and grapefruit), nuts (for example, chestnut, walnuts, hazelnuts, almond, pistachio, cashew nuts and *macadamia* nuts),
berry fruits (for example, blueberry, cranberry, blackberry and raspberry),
grape, kaki, persimmon, olive, Japanese plum, banana, coffee, date palm, coconuts, oil palm and the others;

Trees other than fruit trees:
tea, mulberry,
flowering plant (for example, dwarf azalea, camellia, hydrangea, sasanqua, *Illicium anisatum*; cherry trees, tulip tree, crape myrtle and fragrant olive),
roadside trees (for example, ash, birch, dogwood, *Eucalyptus*, *Ginkgo biloba*, lilac, maple, *Quercus*, poplar, Judas tree, *Liquidambar formosana*, plane tree, zelkova, Japanese arborvitae, fir wood, hemlock, juniper, *Pinus*, *Picea*, *Taxus cuspidate*, elm and Japanese horse chestnut),
*Sweet viburnum*, *Podocarpus macrophyllus*, Japanese cedar, Japanese cypress, croton, Japanese spindletree and *Photinia glabra*);

Lawn:
sods (for example, *Zoysia japonica*, *Zoysia matrella*),
bermudagrasses (for example, *Cynodon dactylon*),
bent glasses (for example, *Agrostis gigantea*, *Agrostis stolonifera*, *Agrostis capillaris*),
blueglasses (for example, *Poa pratensis*, *Poa trivialis*),
festucae (for example, *Festuca arundinacea* Schreb., *Festuca rubra* L. var. *commutata* Gaud., *Festuca rubra* L. var. *genuina* Hack),
ryegrassses (for example, *Lolium multiflorum* Lam, *Lolium perenne* L),
*Dactydis glomerata*, *Phleum pratense*);

Others:
flowers (for example, rose, carnation, chrysanthemum, Eustoma, gypsophila, gerbera, marigold, salvia, petunia, verbena, tulip, aster, gentian, lily, pansy, cyclamen, orchid, lily of the valley, lavender, stock, ornamental cabbage, primula, poinsettia, gladiolus, cattleya, daisy, cymbidium and begonia),
bio-fuel plants (for example, jatropha, safflower, Camelina, switch grass, *Miscanthus giganteus*, *Phalaris arundinacea*, *Arundo donax*, kenaf, cassava, willow), and ornamental foliage plants, and the others.

Among the above-mentioned plants, preferred examples include corn, cotton, soybean, beet, rapeseed and rice.

The above-mentioned "plant" includes plants, to which a resistance has, been conferred by a classical breeding method or genetic engineering technique.

The composition for controlling harmful arthropods of the present invention is used to control harmful arthropods by applying it to the plant or an area for cultivating the plant. Such plants to be used herein include foliages of plant, flowers of plant, fruits of plant, seeds of plant, or bulbs of plant. The bulbs to be used herein are intended to mean bulb, corn, rootstock, tubera, tuberous root and rhizophore.

The method for controlling harmful arthropods of the present invention comprises applying the composition for controlling harmful arthropods of the present invention.

Examples of the method of applying the composition for controlling harmful arthropods of the present invention include, an application to stems and leaves of plants such as a foliage application; an application to seeds of plants; and an application to area for cultivating plants such as a soil treatment and a submerged application.

Specific examples of the application to stems and leaves of plants such as a foliage application in the present invention include an application to surfaces of plants to be cultivated, for example, by a ground application with a manual sprayer, a power sprayer, a boom sprayer or Pancle sprayer or by an aerial application by using manned or unmanned airplane or helicopter.

Specific examples of the application to seeds of plants in the present invention include an application of the composition for controlling harmful arthropods of the present invention to seeds or bulbs of plants, more specifically, a spray coating treatment on the surface of seeds or bulbs, a smear treatment on the seeds or bulbs of plants, an immersion treatment, a film coating treatment and a pellet coating treatment.

Specific examples of the application to area for cultivating plants such as a soil application and submerged application in the present invention include, a planting hole application, a plant foot application, a row application, an in-furrow application, an overall application, a side ditch application, a nursery box application, a nursery bed application, a nursery soil incorporation, a bed soil incorporation, a paste fertilizer incorporation, a paddy water application, and a submerged application under flooding condition.

When the composition for controlling harmful arthropods of the present invention is applied to plants or area for cultivating plants, the application dose varies depending on the kinds of plants to be protected, the species or the degree of emergence of harmful arthropods to be controlled, the dosage form, the timing of application, weather conditions, etc., but the total amount of the present amide compound or salt thereof and the pyrazole compounds is in the range of usually from 0.05 to 10,000 g, preferably from 0.5 to 1,000 g per 1,000 $m^2$ of the area for cultivating plants.

When the composition for controlling harmful arthropods of the present invention is applied to seeds of plants, the application dose varies depending on the kinds of plants to be protected, the species or the degree of emergence of harmful arthropods to be controlled, the dosage form, the timing of application, weather conditions, etc., but the total amount of the present amide compound or salts thereof and the pyrazole compounds is in the range of usually from 0.001 to 100 g, preferably from 0.05 to 50 g per 1 kg of the seeds.

The emulsifiable concentrate, the wettable powder or the flowable formulation, etc. of the composition for controlling harmful arthropods of the present invention is usually applied by diluting it with water, and then spreading it. In this case, the total concentration of the present amide compound or salts thereof and the pyrazole compounds is in the range of usually 0.00001 to 10% by weight, and preferably 0.0001 to 5% by weight. The dust formulation or the granular formulation, etc, is usually applied as itself without diluting it.

EXAMPLES

The following Examples including Formulation examples and Test examples serve to illustrate the present invention in more detail, which should not intend to limit the present invention. In the Examples, the term "part(s)" means part(s) by weight unless otherwise specified, and "the present amide compound (Compound No. X)" corresponds to "Compound No. X" listed in Table 1, that is, for example, "the present amide compound (Compound No. 4)" refers to Compound No. 4 listed in Table 1.

Formulation examples are shown below.

Formulation Example 1

Ten (10) parts of the present amide compound selected from Compound No. 1 to Compound No. 11, 5 parts of chlorantraniliprole, 35 parts of a mixture (weight ratio 1:1) of white carbon and ammonium polyoxyethylene alkyl ether sulfate are mixed with an appropriate amount of water so as to give a total amount of 100 parts, and then the mixture is finely-ground by a wet grinding method to obtain a flowable formulation.

Formulation Example 2

Ten (10) parts of the present amide compound selected from Compound No. 1 to Compound No. 11, 5 parts of cyantraniliprole, 35 parts of a mixture (weight ratio 1:1) of white carbon and ammonium polyoxyethylene alkyl ether sulfate are mixed with an appropriate amount of water so as to give a total amount of 100 parts, and then the mixture is finely-ground by a wet grinding method to obtain a flowable formulation.

Formulation Example 3

Ten (10) parts of the present amide compound selected from Compound No. 1 to Compound No. 11, 5 parts of a compound represented by a formula (II), 35 parts of a mixture (weight ratio 1:1) of white carbon and ammonium polyoxyethylene alkyl ether sulfate are mixed with an appropriate amount of water so as to give a total amount of 100 parts, and then the mixture is finely-ground by a wet grinding method to obtain a flowable formulation.

Formulation Example 4

Ten (10) parts of the present amide compound selected from Compound No. 1 to Compound No. 11, 10 parts of chlorantraniliprole, 1.5 parts of sorbitan trioleate, and 28 parts of an aqueous solution containing 2 parts of polyvinyl alcohol are mixed, and then the mixture is finely-ground by a wet grinding method. To this mixture is added an appropriate amount of aqueous solution containing 0.05 parts of xanthane gum and 0.1 parts of magnesium aluminium silicate so as to give a total amount of 90 parts, and then 10 parts of propylene glycol is added thereto. The mixture is stirred to obtain a flowable formulation.

Formulation Example 5

Ten (10) parts of the present amide compound selected from Compound No. 1 to Compound No. 11, 10 parts of cyantraniliprole, 1.5 parts of sorbitan trioleate, and 28 parts of aqueous solution containing 2 parts of polyvinyl alcohol are mixed, and then the mixture is finely-ground by a wet grinding method. To this mixture is added an an appropriate amount of aqueous solution containing 0.05 parts of xanthane gum and 0.1 parts of magnesium aluminium silicate so as to give a total amount of 90 parts, and then 10 parts of propylene glycol is added thereto. The mixture is stirred to obtain a flowable formulation.

Formulation Example 6

Ten (10) parts of the present amide compound selected from Compound No. 1 to Compound No. 11, 10 parts of a compound represented by a formula (II), 1.5 parts of sorbitan trioleate, and 28 parts of an aqueous solution containing 2 parts of polyvinyl alcohol are mixed, and then the mixture is finely-ground by a wet grinding method. To this mixture is added an appropriate amount of aqueous solution containing 0.05 parts of xanthane gum and 0.1 parts of magnesium aluminium silicate so as to give a total amount of 90 parts, and then 10 parts of propylene glycol is added thereto. The mixture is stirred to obtain a flowable formulation.

Formulation Example 7

Ten (10) parts of the present amide compound selected from Compound No. 1 to Compound No. 11, 20 parts of chlorantraniliprole, 3 parts of calcium lignin sulfonate, 2 parts of sodium lauryl sulfate, and the rest parts of synthetic hydrated silicon oxide are well mixed while grinding to obtain 100 parts of a wettable powder.

Formulation Example 8

Ten (10) parts of the present amide compound selected from Compound No. 1 to Compound No. 11, 20 parts of cyantraniliprole, 3 parts of calcium lignin sulfonate, 2 parts of sodium lauryl sulfate, and the rest parts of synthetic hydrated silicon oxide are well mixed while grinding to obtain 100 parts of a wettable powder.

Formulation Example 9

Ten (10) parts of the present amide compound selected from Compound No. 1 to Compound No. 11, 20 parts of a compound represented by a formula (II), 3 parts of calcium lignin sulfonate, 2 parts of sodium lauryl sulfate, and the rest parts of synthetic hydrated silicon oxide are well mixed while grinding to obtain 100 parts of a wettable powder.

Treatment Example 1

The flowable formulation prepared in Formulation example 1 is used for a smear treatment in an amount of 500 ml per 100 kg of dried sorghum seeds by using a rotary seed treatment machine (seed dresser, produced by Hans-Ulrich Hege GmbH) to obtain the treated seeds.

The seeds treated with each of the flowable formulations prepared in Formulation examples 2 to 6 are obtained in a manner similar to the above, by using the flowable formulations prepared in Formulation examples 2 to instead of the flowable formulation prepared in Formulation example 1.

Treatment Example 2

The flowable formulation prepared in Formulation example 1 is used for a smear treatment in an amount of 40 ml per 10 kg of dried corn seeds by using a rotary seed treatment machine (seed dresser, produced by Hans-Ulrich Hege GmbH) to obtain the treated seeds.

The seeds treated with each of the flowable formulations prepared in Formulation examples 2 to 8 are obtained in a manner similar to the above, by using the flowable formulations prepared in Formulation examples 2 to 6 instead of the flowable formulation prepared in Formulation example 1.

Treatment Example 3

The wettable powder prepared in Formulation example 7 is used for powder coating treatment in an amount of 50 g per 10 kg of dried corn seeds to obtain the treated seeds.

The seeds treated with each of the wettable powders prepared in Formulation examples 10 to 15 are obtained in a manner similar to the above, by using the wettable powders prepared in Formulation examples 8 or 9 instead of the wettable powder prepared in Formulation example 7.

Treatment Example 4

The flowable formulation prepared in Formulation example 1 is used for a smear treatment in an amount of 50 ml per 10 kg of dried soybean seeds by using a rotary seed treatment machine (seed dresser, produced by Hans-Ulrich Hege GmbH) to obtain the treated seeds.

The seeds treated with each of the flowable formulations prepared in Formulation examples 2 to 6 are obtained in a manner similar to the above, by using the flowable formulations prepared in Formulation examples 2 to instead of the flowable formulation prepared in Formulation example 1.

Next, the effect of the present invention is shown in test examples.

Test Example 1

The present amide compound 1.25 mg and the present pyrazole compound 12.5 mg were mixed and thereto were added 150 microliters of slurry that was prepared by mixing 10 parts of Color Coat Red (manufactured by Becker Underwood Inc.: coloring agent), 10 parts of CF-CLEAR (manufactured by Becker Underwood Inc.: spreading agent) and an appropriate amount of water so as to give a total amount of 100 parts and the resulting mixtures were then mixed thoroughly, and the total amount of the mixture was added to 25 grains of corn seeds and the resulting mixtures were then agitated to give treated corn seeds. After air drying, the treated corn seeds were seeded into a 160 ml plastic cup in a ratio of 2 grains per the cup.

At 14 days post the seeding, *Spodoptera litura* at the fourth-instar larval stages were released in a ratio of about 5 heads of insects per the cup, and then the cups were covered with a 540 ml plastic cup (hereinafter, referred to as a "treated area"). At 3 days post the release, the number of surviving larvae in each cup was observed.

On the other hand, the same seeding was carried out using corn seeds without the above-mentioned treatment (hereinafter, referred to as an "untreated area"), and at 3 days post the release, the number of surviving larvae in each cup was observed.

Each of mortality of insects in the treated area and the untreated area was calculated by the following equation 1). The two duplicate tests were performed. The average value is shown in Table 2.

Mortality of insects (%)=(Number of test insects−Number of surviving insects)/Number of test insects×100    Equation 1);

TABLE 2

| Test compounds | Dose (mg/25 grains) | Mortality of Insects (%) |
|---|---|---|
| Present amide compound (Compound No. 1) + chlorantraniliprole | 1.25 + 12.5 | 100 |
| Present amide compound (Compound No. 1) + cyantraniliprole | 1.25 + 12.5 | 100 |
| Present amide compound (Compound No. 3) + chlorantraniliprole | 1.25 + 12.5 | 100 |
| Present amide compound (Compound No. 3) + cyantraniliprole | 1.25 + 12.5 | 100 |
| Present amide compound (Compound No. 4) + chlorantraniliprole | 1.25 + 12.5 | 100 |
| Present amide compound (Compound No. 4) + cyantraniliprole | 1.25 + 12.5 | 100 |
| Present amide compound (Compound No. 8) + chlorantraniliprole | 1.25 + 12.5 | 100 |
| Present amide compound (Compound No. 8) + cyantraniliprole | 1.25 + 12.5 | 100 |
| untreated area | — | 0 |

Test Example 2

The present amide compound 2.5 mg and the present pyrazole compound 2.5 mg were mixed and thereto were added 150 microliters of slurry that was prepared by mixing 10 parts of Color Coat Red (manufactured by Becker Underwood Inc.: coloring agent), 10 parts of CF-CLEAR (manufactured by Becker Underwood Inc.: spreading agent) and an appropriate amount of water so as to give a total amount of 100 parts and the resulting mixtures were then mixed thoroughly, and the total amount of the mixture was added to 25 grains of corn seeds and the resulting mixtures were then agitated to give treated corn seeds. After air drying, the treated corn seeds were seeded into a 160 ml plastic cup in a ratio of 2 grains per the cup.

At 14 days post the seeding, *Spodoptera litura* at the fourth-instar larval stages were released in a ratio of about 5 heads of insects per the cup, and then the cups were covered with a 540 ml plastic cup (hereinafter, referred to as a "treated area"). At 3 days post the release, the number of surviving larvae in each cup was observed.

Each of mortality of insects in the treated area was calculated by the following equation 1). The two duplicate tests were performed. The average value is shown in Table 3.

TABLE 3

| Test compounds | Dose (mg/25 grains) | Mortality of Insects (%) |
| --- | --- | --- |
| Present amide compound (Compound No. 3) + chlorantraniliprole | 2.5 + 2.5 | 100 |
| Present amide compound (Compound No. 3) + cyantraniliprole | 2.5 + 2.5 | 100 |
| Present amide compound (Compound No. 4) + cyantraniliprole | 2.5 + 2.5 | 100 |

The invention claimed is:

1. A composition for controlling harmful arthropods comprising an amide represented by a formula (I);

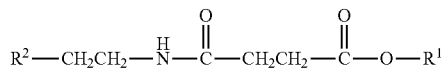

(I)

$R^1$ represents a C1-C6 alkyl group;

$R^2$ represents an optionally substituted phenyl group, and the phenyl group represented by the $R^2$ may be substituted on the carbon atoms independently of each other with one or more substituents selected from a halogen atom, a hydroxyl group, a nitro group, a C1-C6 alkyl group or a C1-C6 alkoxy group;

or salts thereof and at least one pyrazole compound selected from the group (A) consisting of chlorantraniliprole and cyantraniliprole, wherein a weight ratio of the amide compound or salts thereof to the at least one pyrazole compound selected from the group (A) is in the range of 10:1 to 1:10.

2. A method for controlling harmful arthropods which comprises applying an effective amount of the composition for controlling harmful arthropods according to claim 1 to harmful arthropods or a place where the harmful arthropods live.

3. A method for controlling harmful arthropods which comprises applying an effective amount of the composition for controlling harmful arthropods according to claim 1 to plant seeds.

4. The method for controlling harmful arthropods according to claim 3 wherein the plant seeds are seeds of corn, cotton, soybean, beet, rapeseed or rice.

\* \* \* \* \*